(12) United States Patent
White (10) Patent No.: US 8,802,421 B2
(45) Date of Patent: Aug. 12, 2014

(54) METHOD OF PROPAGATING AND DELIVERING YEAST

(75) Inventor: Chris White, San Diego, CA (US)

(73) Assignee: White Labs, San Diego, CA (US)

( * ) Notice: Subject to any disclaimer, the term of this patent is extended or adjusted under 35 U.S.C. 154(b) by 280 days.

(21) Appl. No.: 13/152,207

(22) Filed: Jun. 2, 2011

(65) Prior Publication Data

US 2012/0309076 A1    Dec. 6, 2012

(51) Int. Cl.
| | |
|---|---|
| *C12N 1/00* | (2006.01) |
| *C12M 1/02* | (2006.01) |
| *C12M 1/00* | (2006.01) |
| *C12M 1/12* | (2006.01) |
| *C12M 1/36* | (2006.01) |
| *C12M 1/26* | (2006.01) |

(52) U.S. Cl.
CPC .............. *C12M 23/14* (2013.01); *C12M 41/22* (2013.01); *C12M 23/40* (2013.01); *C12M 37/04* (2013.01); *C12M 41/48* (2013.01); *C12M 33/22* (2013.01)
USPC .................................. 435/255.21; 435/255.1

(58) Field of Classification Search
None
See application file for complete search history.

(56) References Cited

U.S. PATENT DOCUMENTS

| | | | |
|---|---|---|---|
| 3,946,780 A | | 3/1976 | Sellers |
| 4,063,383 A | | 12/1977 | Green |
| 4,708,938 A | | 11/1987 | Hickinbotham |
| 5,225,346 A | * | 7/1993 | Matsumiya et al. ....... 435/289.1 |
| 5,789,147 A | * | 8/1998 | Rubinstein et al. ............... 435/2 |

FOREIGN PATENT DOCUMENTS

CA    1228767    11/1987

OTHER PUBLICATIONS

Mikola et al. "Evaluation of a novel Wave Bioreactor cellbag for aerobic yeast cultivation" Bioprocess Biosyst Eng (2007) 30:231-241.*
Lodolo et al. "The yeast *Saccharomyces cerevisiae* themain character in beer brewing" FEMS Yeast Res 8 (2008) 1018-1036.*
Van der Stahl Scientfic "Heat Sealing Machines" www.wnderstahl.comlheat-sealing-machines-explained/ available online Apr. 24, 2010, 1pg.*
Walsh et al. "Growth of *Saccharomyces cerevisiae* and *Saccharomyces uvarum* in a Temperature Gradient Incubator" J. Inst. Brew., May-Jun. 1977, vol. 83, pp. 169-112.*
van Hamersveld et al. "Quantification of Brewers' Yeast Flocculation in a Stirred Tank: Effect of Physical Parameters on Flocculation" Biotechnology and Bioengineering, vol. 56, No. 2, Oct. 20, 1997, pp. 190-200.*
GE Healthcare "WAVE Bioreactor 2/10 and 20/50 systems" 8pgs, first published Feb. 2009.*

* cited by examiner

*Primary Examiner* — Thane Underdahl
(74) *Attorney, Agent, or Firm* — Temmerman Law Office; Mathew J. Temmerman (57) ABSTRACT

A method of propagating, concentrating and delivering yeast is disclosed. The method comprises the steps of producing and inoculating a bag, propagating yeast within the bag, and concentrating the yeast in a section of the bag that is the removed from the remainder of the bag while not exposing any portion of the yeast therein to an external environment. In order to remove the bag, which contains the most concentrated slurry of yeast, a smaller bag is heat-sealed off of the larger bag, thereby creating a separate bag for the living sediment, which is still the bag in which the sediment was propagated. In a preferred embodiment, the method is specific to the alcoholic beverage industry. The method is also applicable to other industries that grow and transport yeast, bacteria, molds and other microorganisms.

12 Claims, 7 Drawing Sheets

METHOD OF PROPAGATING AND DELIVERING YEAST

BACKGROUND

1. Field of the Invention

The present invention relates to the propagation, preparation for transport, transport, and delivery of live yeast, and in particular to the preparation and shipping of a container of concentrated yeast slurry or sediment, the container portioned off from a larger container in which the yeast was grown so as to protect the yeast from contamination by the external environment.

2. General Background and Description of Related Art

Mankind has practiced brewing since Neolithic times. Evidence of beer making has been found in the earliest writings of recorded history. Common to all brewing processes is the use of yeast and/or bacteria which multiply quickly and which ferment carbohydrates into alcohols and carbon dioxide. Yeast is essential in the production of beer, wine, spirits, and bread. Yeasts are amongst the simplest living organisms, and readily grow on moist surfaces and in liquids that are rich in nutrients.

During the standard brewing process, grain is first malted to help release the starches contained within the grain and to enzymatically convert those starches into fermentable sugars. Subsequently the malted grain is milled or cracked and then mashed to extract the sugars into a water solution called wort. During the mashing process the wort is boiled to remove excess water, to denature the starch-breaking enzymes, and to sterilize the wort. Optionally, the wort may then be boiled with hops, herbs, or additional sugars to impart flavor, color, and aroma. The wort is then cooled to a temperature at which yeast can be added, and the wort is inoculated with pure yeast. These yeast multiply quickly and ferment the sugars into alcohols and carbon dioxide. It is important that the yeast added to the wort is very pure, and that contamination is avoided because any unintended microorganisms entering the nutrient rich wort will easily multiply and impart undesirable flavors and/or disturb the brewing process. By the end of the fermentation period, the yeast settles to the bottom of the fermenter in a slurry or sediment layer.

There are myriad types of yeast used in brewing, and type of yeast selected influences the character and flavor of the final product. Regardless of the yeast chosen, or the mixture of yeasts chosen, adding yeast that is free from contamination is important due to the aforementioned consequences of contamination by unintended microorganisms. There is thus a need for pure yeast cultures.

Like the process of fermentation described above, the propagation of pure yeast is a delicate process requiring specific temperatures, air and nutrient supply, and a complete lack of contamination. Problems arise when batches of yeast prepared for sale or use are discarded because they are contaminated during the yeast-propagating process. Unlike the process of fermentation described above, where the finished product is the alcoholic byproduct of the years metabolism, the finished product in the present yeast culture preparation is the pure yeast itself, rather than the alcoholic byproduct of the yeast metabolism.

Thus, yeast production facilities strive to be extremely clean and to avoid contamination at all costs. Such production facilities have developed many means, techniques, and protocols to minimize the risk of contamination. It is beyond the scope of this disclosure to discuss all such past innovations, however, some of the prior art means, techniques, and protocols most relevant to the current application are described below.

It is known in the pharmaceutical industry to grow cultures in-situ in plastic bags or containers and then to ship the culture in those same containers. Because the bags or containers are never opened, this technique offers increased sterility and decreased opportunity for contamination. The downside to this technique is that bags of yeast propagated in this manner often contain only a small amount of concentrated yeast and a large amount of less valuable liquid. As brewers typically require large amounts of concentrated yeast, the shipment of huge quantities of less valuable liquids is wasteful at best, and at worst impracticable. There is currently no way to separate the concentrated and valuable yeast from the less valuable liquid taking up the majority of the volume of the container. Thus, there is a need to separate out the concentrated yeast whilst not subjecting the contents of the fermenter to contamination from the environment.

U.S. Pat. No. 3,946,780 discloses a simple plastic bag fermentation container with a one-way valve to allow fermentation gasses to pass out of the container while not allowing bacteria or other contaminants to enter. This bag does not include a means for concentrating the yeast grown therein and further does not completely isolate the yeast from the environment. Moreover, the '780 patent relates to the fermenting of yeast, where the desired product to be output from the system is alcohol in a medium. In processes such as the '780 patent, the sediment of yeast is often discarded while the liquid phase is sold or used in additional processes.

U.S. Pat. No. 4,063,383 discloses a sterile bag to which a user adds mushroom spores and growth medium. The user then seals the bag and lets the spores grow to a state at which the sealed bag may be sold and/or shipped to others who want to grow mushrooms. This bag allows transpiration and does not provide a means for concentrating the contents of the bag subsequent to the growth stage. The '383 patent fails to describe or teach a method of providing a concentrated amount of spores or yeast in a bag that does not allow growth during transport. Preventing further growth during transport is important when shipping a highly concentrated bag, because any growth therein could cause the bag to inflate or explode during shipping.

U.S. Pat. No. 4,708,938 discloses a method of making yeast through alcoholic fermentation within a closed system wherein externally applied pressure causes the fermented liquid to be expelled from a first bag and into a smaller bag. This system separates the yeast from the external environment but is needlessly complicated, increasing both the cost and risk of contamination. Further, this system is related to the separation of beer from the contaminated yeast.

Canadian Pat. No. 1228767 shows the use of heat-sealing to package baker's yeast. In this instance, yeast is placed in a package that is then completely sealed and thus rendered nearly impervious to oxygen, carbon dioxide, and water vapor. A small amount of carbon dioxide metabolizes out from the yeast, generating a protective cushion around the yeast in the bag. A method of separating a concentrated portion of the contents of the bag is not disclosed. Moreover, this device merely provides a container capable of absorbing a small amount of growth and gas generation. The publication does not describe a container that is aerated so as to induce large amounts of growth nor does it describe the portioning off of a smaller container of concentrated yeast. Finally, this patent concerns a dry yeast, and accordingly has a much longer shelf life and a lesser need for temperature regulation.

All of the above prior art suffers from one or more of the following limitations or deficiencies: the production or shipping of a concentrated liquid yeast culture in a section of a bag in which it was grown and separated out from while preventing contamination by the external environment, a mechanism that provides for vigorous aeration of the yeast in order to promote growth, and a way to separate out a concentrated quantity of yeast growth without risk of contamination.

It is thus a first object of the present invention to prepare and ship a container in which live liquid yeast is propagated and concentrated while being protected from external environment contamination.

It is a further object of the invention to decrease shipping costs by concentrating propagated liquid yeast in a bag that allows no venting or contamination during or prior to shipping.

It is a further object of the invention to decrease the difficulty and risk of contamination in propagating, handling, and shipping yeast.

It is a still further object of the invention to accurately assess the concentration of liquid yeast in a bag through noninvasive sampling of the yeast before shipping.

These and other objects, advantages, features and aspects of the present invention will become apparent as the following description proceeds. To the accomplishment of the foregoing and related ends, the invention, then, comprises the features hereinafter more fully described and particularly pointed out in the claims, the following description and the annexed drawings setting forth in detail certain illustrative embodiments of the invention, these being indicative, however, of but several of the various ways in which the principles of the invention may be employed.

SUMMARY OF THE INVENTION

This application presents a method for propagating, concentrating, and delivering live yeast. The method comprises the step of providing a sterile bag for the propagation of yeast wherein the yeast concentrates in a section of the bag, which is then separated from the remainder of the bag whilst not exposing any portion of the yeast therein to the external environment.

In the preferred embodiment the concentrated yeast is separated from the rest of the solution through a heat-sealing method thereby eliminating exposure to the external environment. In an exemplary embodiment, 2-liters of concentrated yeast growth slurry is separated from a 50-liter bag through a compression and heat-sealing method. In this method, the bag is squeezed to separate the smaller section of the back containing the concentrated yeast sediment from the upper remaining section of the bag, and then in a single action the smaller bag is partitioned off through heat-sealing. During this procedure the internal contents of the bag are never exposed to the outside environment.

BRIEF DESCRIPTION OF THE DRAWINGS

The foregoing aspects and many of the attendant advantages of the invention will become more readily appreciated as the same becomes better understood by reference to the following detailed description, when taken in conjunction with the accompanying drawings, wherein.

DETAILED DESCRIPTION OF THE INVENTION

The following description is presented to enable a person of ordinary skill in the art to make and use various aspects and examples of the present invention. Descriptions of specific materials, techniques, and applications are provided only as examples. Various modifications to the examples described herein will be readily apparent to those of ordinary skill in the art, and the general principles defined herein may be applied to other examples and applications without departing from the spirit and scope of the invention. Thus, the present invention is not intended to be limited to the examples described and shown, but is to be accorded the scope consistent with the appended claims.

The Applicant discloses a modular multi-bag propagation unit to facilitate easy handling of the process elements and efficient use of equipment, services and resources for small-scale liquid yeast production. In a preferred embodiment of the invention the yeast may be transported and used for beer production. The equipment and method accomplish and comprise the steps of producing and inoculating a bag while keeping the bag free from all contaminants, propagating yeast within the bag, and concentrating the yeast in a section of the bag that is then removed from the remainder of the bag whilst not exposing any portion of the yeast therein to an external environment. In order to remove only the section of the bag containing the most concentrated slurry of yeast, a smaller bag is heat-sealed off of the larger bag. An advantage of the invention is that the yeast may be propagated in the very bag in which it is transferred to the purchaser, thus reducing the risk of contamination.

Figure 1:
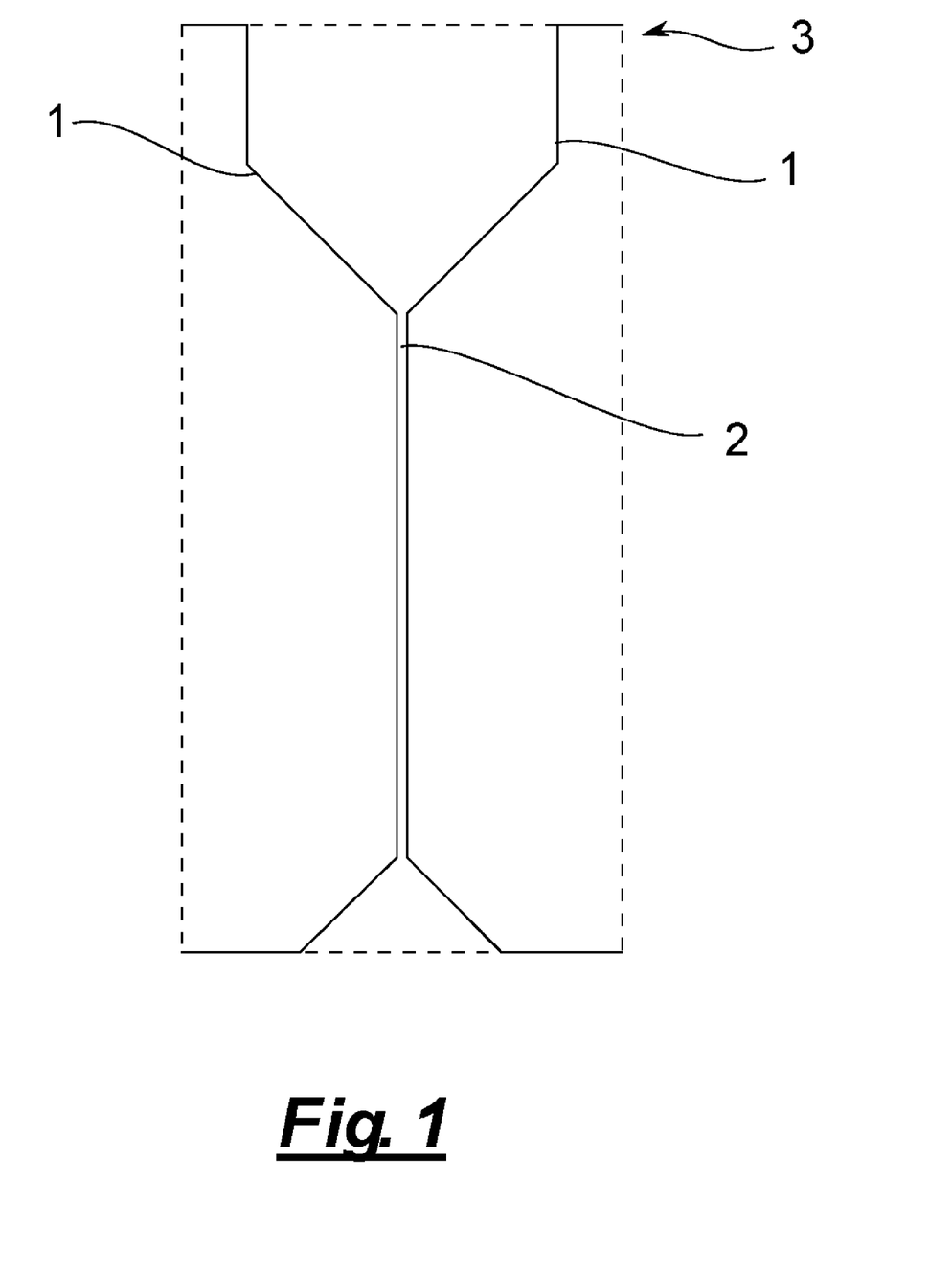
FIG. 1 is a diagram of a platen used for the initial heat seal wherein the bag is formed, according to the preferred embodiment of the invention.
Figure 2:
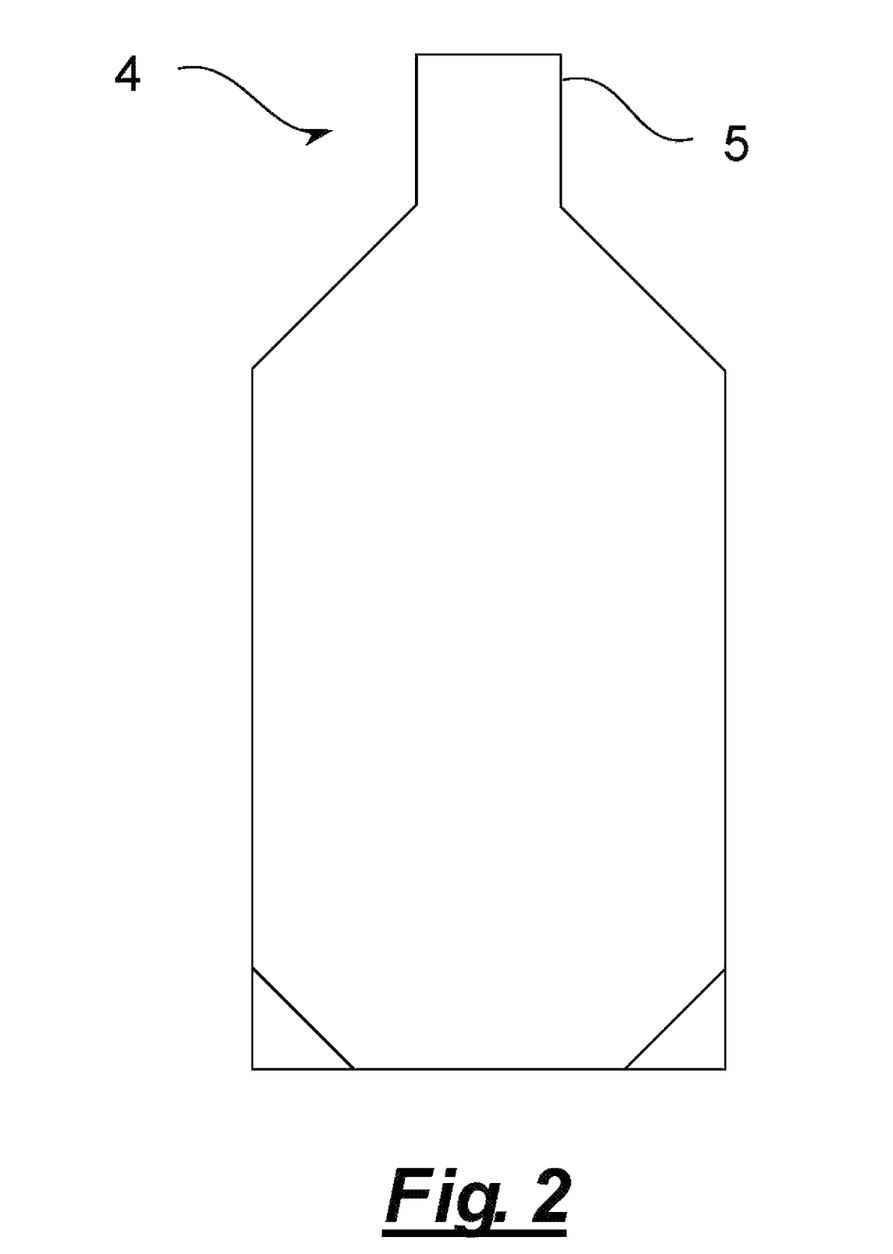
FIG. 2 is a drawing of a bag made by use of the platen.

Turning first to FIGS. 1 and 2, in use, the Applicant's method may include an initial heat-sealing step, wherein the sealed sterile bags 4 to be inoculated are produced. The bags 4 are produced in this exemplary embodiment from an ordinary plastic material. In this first heat-sealing step, plastic sheeting is pulled off a tubular roll of polyethylene and heat sealed into four compartments using a custom made platen 3 forming the shape of four bags. The custom made platen 3 comprises at least one heat-sealing feature 1 which creates a welded bond 5 between layers of polyethylene. The custom made platen 3 further comprises a gap 2 between a first and a second heat-sealing features 1. In one embodiment the bags 4 created have a capacity of 50-liters nominal volume. Bags of larger or smaller size may be possible with appropriate equipment scaling.

Figures 3A, 3B:
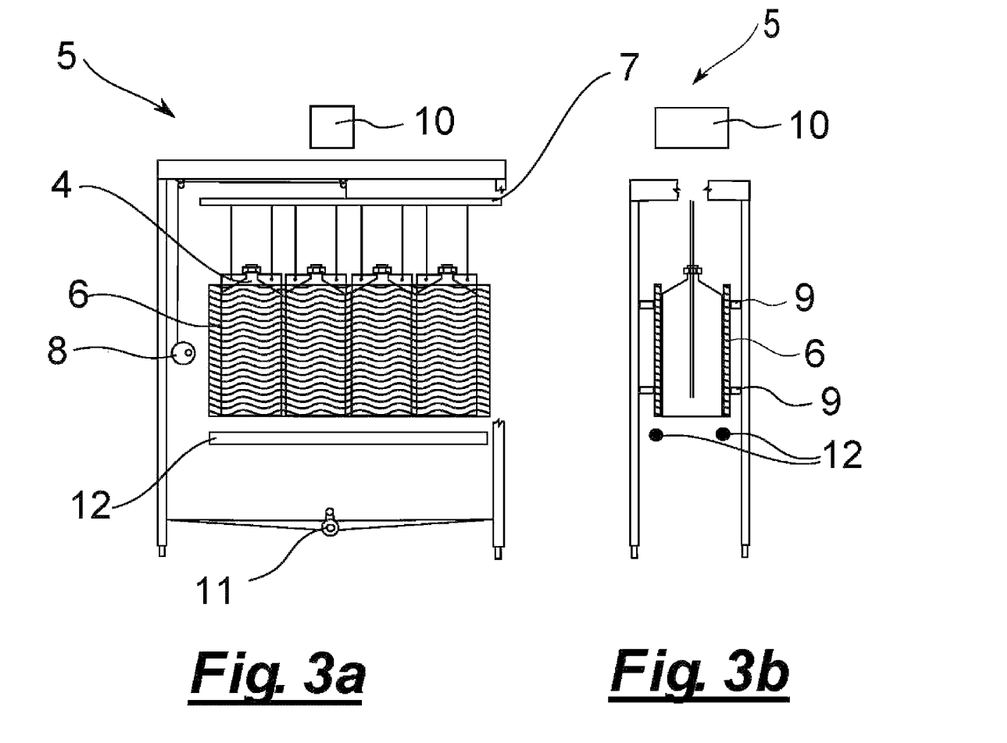
FIG. 3a and FIG. 3b is a diagram of four bags installed in a skid rack, the diagram depicting a front view (3a) and a side view (3b)

FIGS. 3a & 3b depict front and side views of an exemplary embodiment in which four sealed bags 4 may be formed at one time as a set. The four co-joined bag set may be installed into a skid unit 5 as a set and suspended between cooling panels 6 from a carrier bar 7, which is controlled by a winch 8 or other similar means. The bags 4 are sealed and sterile when fitted on the skid unit. The cooling panels 6 press against the bags 4 by means of hydraulic, pneumatic, or other compression means 9. The bags may be connected to dedicated sterile bag fittings (not labeled in FIG. 3a and FIG. 3b), having flexible hoses (not shown) which in turn may be connected to valve manifolds 10 for air and $CO_2$ services and for hot wort supply. The bag fitting used allows air in, wort/medium in, gas out, and leaves room for a temperature probe and an inoculation port, thereby giving the bag the same stainless steel connections and ports one would find on a conventional propagation tank. The skid unit may also comprise a trough and drain 11. Also shown in FIG. 3a and FIG. 3b is the heat-sealing mechanism 12 which will be discussed in below.

Figure 4:
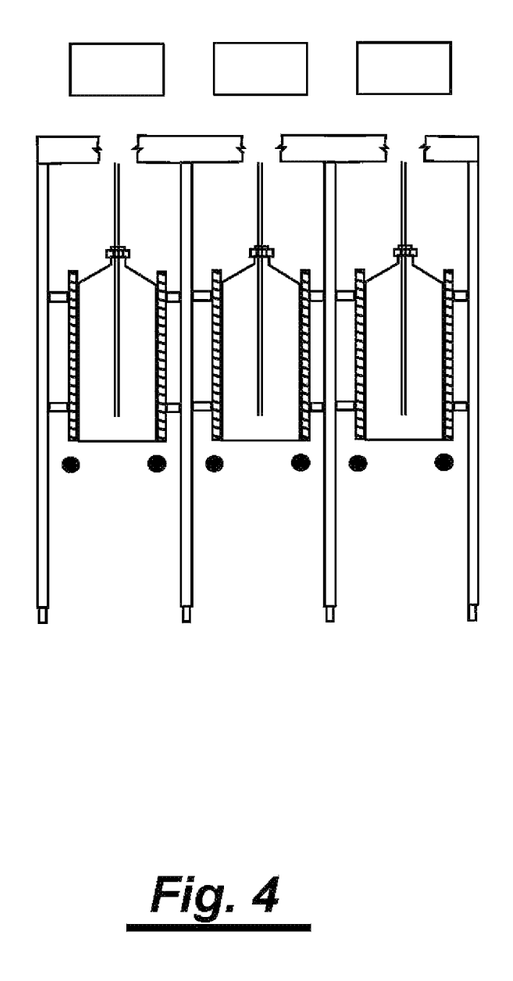
FIG. 4 is a side view of a twelve bag skid rack system according to an alternative embodiment of the invention.

Turning to FIG. 4, an exemplary configuration of the four co-joined bag set discussed above is depicted. In this configuration three four-bag modules are used in three adjoining skids for a total of twelve bags. The system may be extended in modules of 4-bag units.

Figure 5:
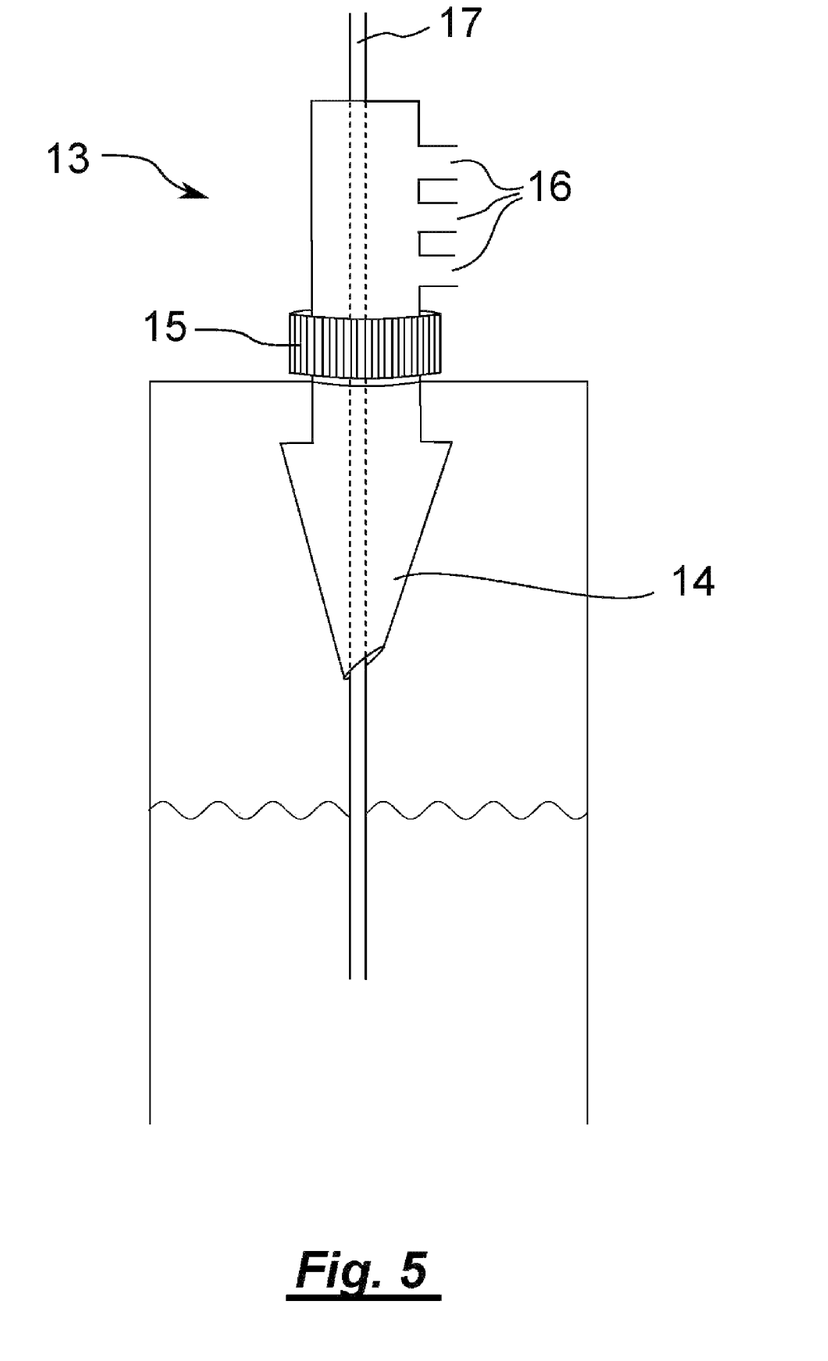
FIG. 5 is a diagram of the sterile bag fitting attached to a bag showing how a bag may be filled, inoculated, provided with air, and provided an outlet for gas venting according to the preferred embodiment of the invention.

Turning now to FIG. 5, the bag fitting and related processes are depicted. Here, using a sterilized needle (not shown) the operator pierces the top of the bag 4 and aseptically inserts the conical portion 14 of the sterile bag fitting 13 as shown. The elastic bag material expands as the bag fitting is pushed through the initial needle hole. Due to the inherent elasticity of the bag, the needle hole contracts once the conical portion 14 of the bag fitting is pushed all the way through. At this stage the bag 4 is air tight at normal atmospheric pressures, but to prevent the airtight seal from being lost under pressure during operation, the components are secured more tightly together by tightening a compression nut 15. To further ensure sterility, steam may be used to inflate the bag and ensure sterilization of the bag and bag fitting. The top of the bag fitting 13 serves as a manifold and provides pathways for automated bag filling, introduction of air, inoculation and gas exhaust via ports 16 to which hoses (not shown) are attached. Aeration takes place via a sterile, flexible tube 17 that is aseptically inserted vertically inside the bag fitting as shown in FIG. 5. The bottom of the air dip tube 17 is dipped below the liquid level inside the bag. The hoses described may have quick connect fittings to facilitate hookup.

Figure 6:
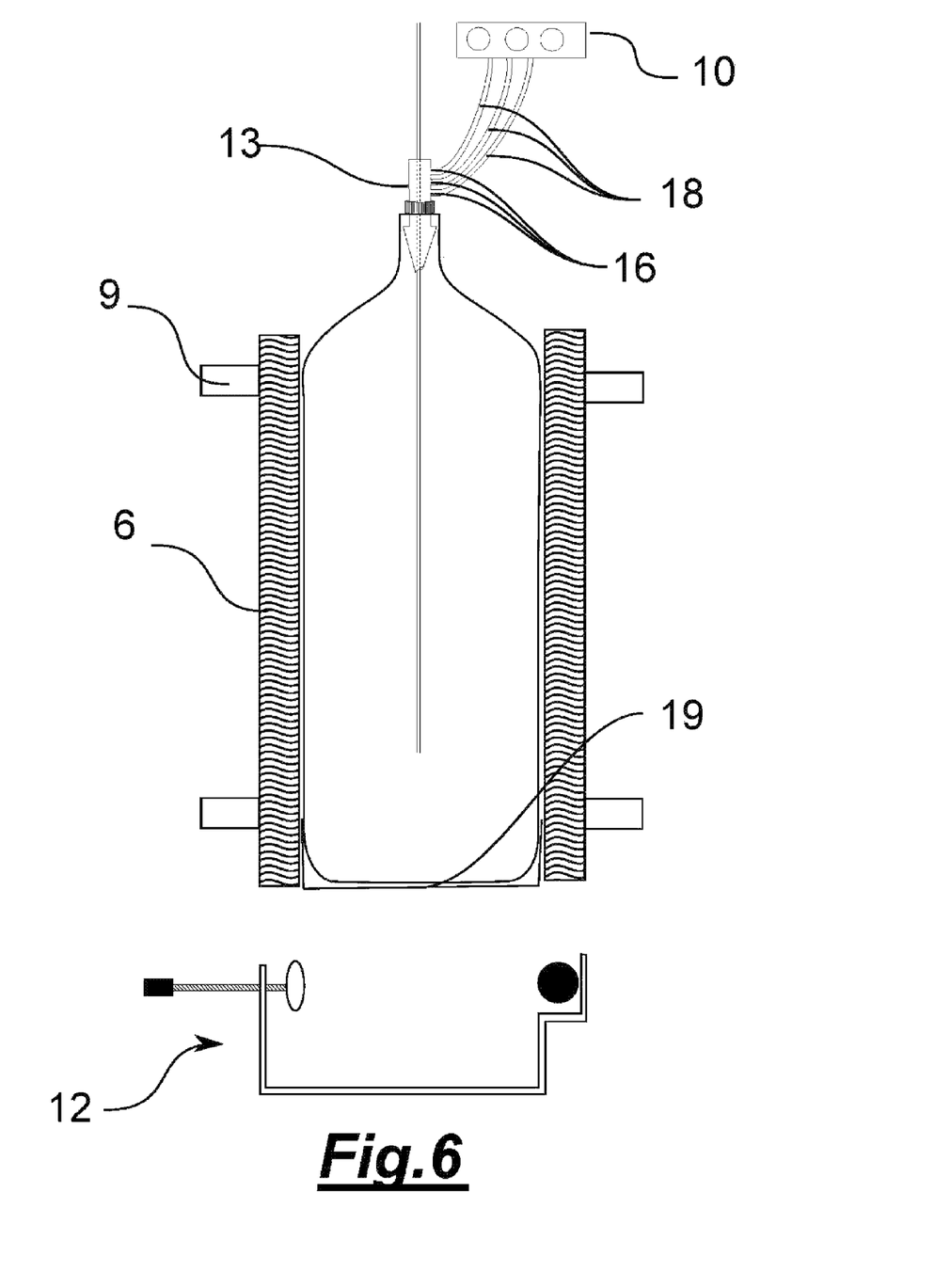
FIG. 6 is a schematic of one bag with sterile bag fitting attached by a plurality of hoses to a valve manifold, cooling panels, according to the preferred embodiment of the invention, and an illustrative heat-sealing mechanism.

Turning to FIG. 6, additional detail regarding the connection between the bag 4, the bag fitting 13, and the skid unit is depicted. Cooling may be supplied to the bag by cooling panels 6, which may be panel type radiators. The cooling panels 6 may squeeze the bag via pneumatic, hydraulic, or other compression means 9 in order to maximize surface contact and transfer of heat. A control loop from an in-bag temperature transmitter (not shown) may monitor the temperature. A sliding plate 19 may lightly support the bag from below and the carrier bar (not shown) may keep the bags upright. As shown the ports 16 are connected by hoses 18 to a valve manifold 10.

Also shown in FIG. 6 is a schematic view of an alternative embodiment of the separation and heat-sealing mechanism 12. In this embodiment the bag is first lowered relative to the cooling panels 6 and then is squeezed by into contact with heat-sealing means, which seals and separates a small section of the bag in which the yeast has been concentrated.

Figure 7:
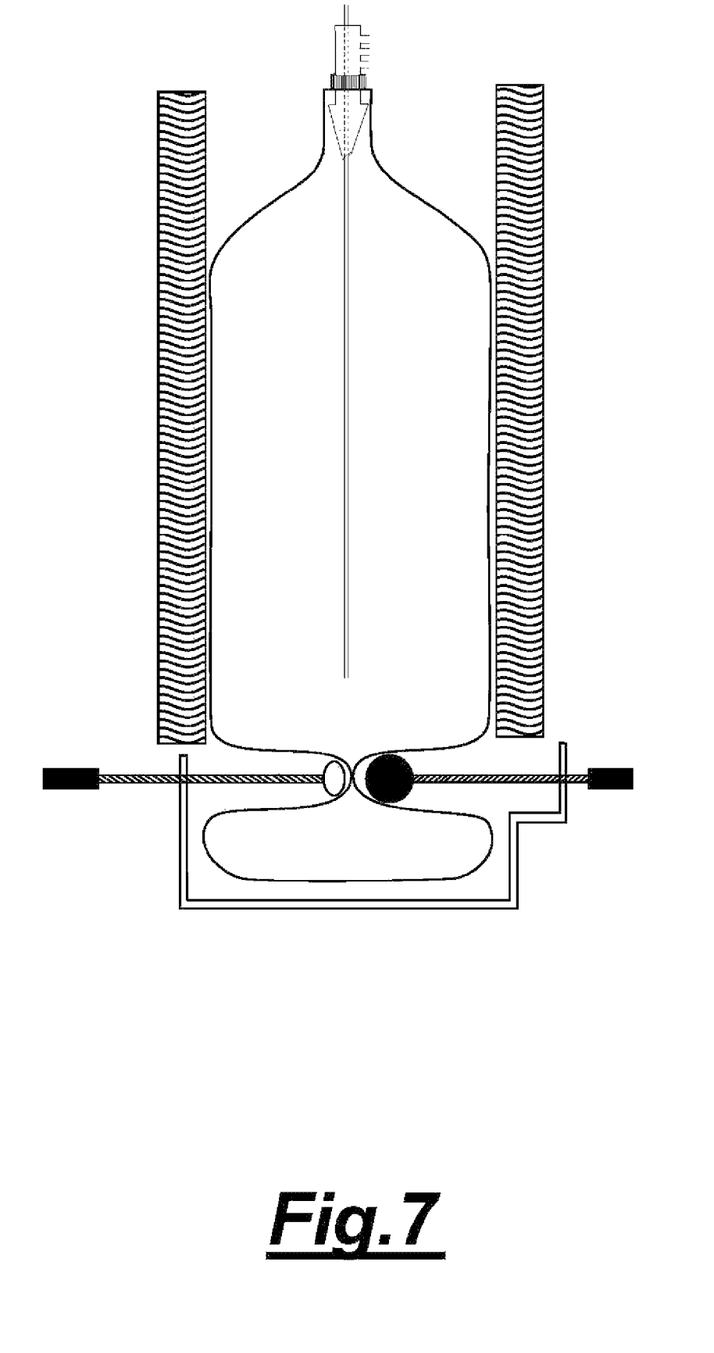
FIG. 7 is a schematic of an illustrative heat-sealing mechanism during the heat sealing step in the Applicant's method.

Turning to FIG. 7, a schematic view of this alternative embodiment of the separation and heat-sealing mechanism is shown in the process of squeezing the bag and heat-sealing off a small section of the bag in which the yeast has been concentrated.

It is to be understood that the separation and heat-sealing mechanism or means disclosed and claimed in this application may be any such means known in the art. These means include but are not limited to mechanisms which squeeze, compress, or apply pressure by use of one or more hydraulic, pneumatic, electrical, or mechanical apparatuses, and that seal off a small section of the bag by use of heating elements, chemical processes, or welding. The separation and heat-sealing mechanism may additionally comprise a cutting means such as, but not limited to, a blade or heat cutter. In an exemplary embodiment the bag is gently squeezed from below so as not to puncture it, nor even to disturb the yeast sediment. Regardless of the mechanism used, the small section of the bag is separated from the upper remaining section of the bag and both the lower, small section and the upper remaining section of the bag are sealed during the same process, if not simultaneously. Thus the contents of both bags are never exposed to the outside environment.

Still other means of removing a section of the bag while preventing exposure to contaminants are considered. For instance, if the bag used were significantly longer than wide, a traditional sausage clip action may be used. Here, the lower, small section of the bag may be twisted and two small flat metal clips may be applied to the twisted area. Cutting between the two clips physically separates the two sections of the bag. Other means for noninvasively separating the lower, small section of the bag from the remainder of the bag are considered.

The skid unit described above may in a preferred embodiment be installed in a brewery as a standalone unit requiring electrical power and utility services. As may be appreciated, there are no interlocks or handshakes required with existing brewery plant equipment, thus the chance for contamination is further reduced. The CIP (cleaning in place) or SIP (sterilization in place) systems will, in one embodiment, be supplied by the brewery and connected manually to the skid with a sequence run by the brewery. The small parts (i.e. bag closures, silicone tubing, and the like) may be sanitized in an industrial washing machine, or by hand, or may be autoclaved. In another embodiment the equipment may be used as a standalone system independent of a brewery.

The CIP as described above is, in a preferred embodiment, designed to work with the bag fitting 13 shown in FIG. 5. During cleaning, the bag fitting is inserted into a conical slot on the CIP station and clamped, allowing thorough CIP/SIP between uses. The CIP/SIP cycle is a completely closed circuit.

Automation of the skid unit may be provided by way of an HMI (human machine interface) and PLC (programmable logic controller) to reduce manual activities. The operator can select fermentation bags and set control parameters for temperature. The installation facility preferably supplies air, coolant and electrical services, and Wort. Optionally, sterile nutrients or enzymes may be added aseptically to the solution at any stage of the process.

The unit in an exemplary embodiment has a PLC/HMI control panel. The PLC/HMI can be used for selecting wort valves and recording information as well as for controlling the temperature. Automatic valves may be wired to this electrical panel, which may also contain pneumatic or hydraulic circuitry.

In an exemplary embodiment the operation of the system is as follows:
   a. A pre-formed set of four 50 liter sealed bags is installed and suspended on a hanger between the cooling panels. Each bag is properly unfurled and rests on the support plate.
   b. A conical sterile bag fitting is connected to each bag as described above, and serves as a manifold, providing pathways for automatic bag filling, inoculation, and for the exhaust of gas generated during the entire process. These connections allow passage for Wort, air, CO2, and yeast. A standard triclamp 1-inch fitting may be inserted into the empty bag and connected to hoses with sterile disk filters.

c. The air valves on the bags are manually opened, and a master air valve is opened to inflate each 4-bag set. Once inflated, the master air valve is closed.

d. Wort valves are selected and a master wort valve is opened, pumping hot wort into each of the bags. Preferably the hot wort is approximately 80 degrees Celsius. Four bags may be filled simultaneously from a selection at the PLC.

e. After a set time sufficient to fill four 50-liter bags, the hot wort valves close automatically.

f. The master valve opens automatically and begins air mixing throughout the bags. Flow is regulated through a rotometer. The flexible air dip tube allows the forcing of air through this pathway for aeration purposes. There are no CO2 exhaust valves, and instead gas pressure is released to atmosphere via the CO2 manifold.

g. Steps a-f are repeated for the next two 4-bag sets.

h. Cool water is circulated through the cooling panels, reducing the temperature of the wort. When the temperature inside the bags of a 4-bag set cools from 80 degrees Celsius to 25 degrees Celsius ("first stage cooling"), the system is prepped for inoculation.

i. Through a special nozzle on the bag fitting, each bag is inoculated with a yeast culture. The yeast introduced into the bag is preferably first cultured from a seed yeast in a laboratory. Numerous strains may be processed in this system simultaneously. The injection step is preferably performed manually, and the operation is logged on the PLC for later labeling and recording of the yeast strain.

j. The temperature of the cooling panels is kept constant as the temperature in the bags rises during the yeast propagation and fermentation process. The cooling panels operate on a temperature control loop in order to maintain the yeast at a predetermined temperature during the process. Preferably, the temperature is detected through a temperature probe attached to one bag of a four-bag set. Preferably, the cooling panels are circulated with ice water and squeeze the bags for maximum surface contact and heat transfer.

k. After predetermined amount of time allotted for fermentation, generally approximately 48 hours, the fermentation process is retarded and stopped by gradually lowering the temperature of the bags to 3 degrees Celsius ("second stage cooling") over a period of 12 hours, and by closing off the supply of oxygen. In other embodiments the second stage cooling may occur more quickly or more slowly. At this point the yeast will concentrate by settling in a slurry at the bottom of the bag, all sugars in the wort have now been consumed and the yeast cells are dormant in a stationary phase. Preferably, the yeast concentrates under the force of gravity l. Once the bags reach 3 degrees Celsius, all remaining air valves (such as the CO2 exhaust valve) are closed, as are other connections to the bag, thereby isolating the contents of the bag from the external environment. Prior to this step and after the inoculation of the yeast, the only connections were through the air inlet and outlet, which provides little chance for contamination.

m. Bottom support for and side panel compression of the bag is removed and the bag slides downwards on a lowering system without disturbing the yeast inside.

n. The bag is then divided into a small section at the lower end of the bag and an upper section of the bag in the vertical plane by a separation and heat-sealing means. In this process, the separation and heat-sealing means squeeze the bag to separate the small section of the yeast-sediment containing bag from the remainder of the bag, and in the same action that small section of the bag is heat-sealed and cut away from the upper remaining section of the bag. The yeast mass is now isolated and sealed into the lower small section of the bag. The bag is labeled and taken to a cold room where it is kept cool and protected from UV light until shipped. The upper remaining bag section and its contents are discarded.

The heat-sealing method will now be described in greater detail. Once approximately 2 liters of yeast sediment are present and concentrated at the bottom of the 50-liter bags, the bags may be cooled and lowered as described generally above. This exposes the bottoms of the bags underneath the cooling panels. The bottom part of each bag comprises sediment (yeast pack/yeast slurry) and is separated as described above, leaving approximately 48 liters of liquid in the upper bag, 2 liters of yeast in the lower, smaller section of the bag. This separation and heat-sealing process occurs without exposing the contents to any source of contamination from the surrounding environment.

As described above, the bags may be joined to one another at their sides. In this embodiment, four bags may be lowered at the same time. In this case, the space between neighboring bags is cut, allowing space for the heat-sealing equipment to reach over, seal and cut off pouches of approximately 2 liters in size, containing the yeast sediment.

After preparation, the relatively small, concentrated bags of yeast are shipped such that there is no, or at most very little, further gas evolution by the yeast. At the time of shipping the final sealed bags do not allow venting, and the cells are in a stationary phase with no sugars to metabolize. This prevents problems that would occur if the concentrated yeast sediment contained in the bags were to produce gas, and subsequently inflate or explode the bags. The yeast delivered in an exemplary embodiment has a moisture content of between 85-90%, lending it the term liquid yeast, which has been shown to give better results in brewing than dry yeast.

As a quality control measure, during the heat-sealing step a small corner portion of the small section of the bag containing concentrated yeast may be heat sealed off and used as a sample for evaluation. Just as in the heat-sealing method, this step is completed without exposing the yeast to the outside environment. In the preferred embodiment of the invention, a portion of every bag is obtained by heat-sealing off a small portion of the bag. Sampling during the growth period may be accomplished by a hand held device that seals off a small portion cut from the main bag or a section of it, or by sealing off a thin strip portion from the bottom of the hanging bag using the same heat sealing machine as used for the separation step. Using the same technique on the small 2 L yeast bag after the final step, a sample may be kept of every lot/bag for final product quality control and record keeping for future lot tracing.

Although the application above has been described with some steps automated and some steps performed manually by an operator, there is no requirement that man or machine perform any particular step. Finally, although in the preferred embodiment of the invention, the invention has been described for use with yeast for beer production, in an alternative embodiment other yeast may be used (such as wine yeast or distiller's yeast) for production of other alcoholic beverages, or yeast may be produced for the baking industry.

Although the invention has been shown and described with respect to certain embodiments, it is obvious that equivalent alterations and modifications will occur to others skilled in the art upon the reading and understanding of the specification. In particular, with regard to the various functions performed by the above-described components, the terms (including any reference to a "means") used to describe such components are intended to correspond, unless otherwise indicated, to any component which performs the specified function of the described component (e.g., that is functionally equivalent) even though not structurally equivalent to the disclosed component which performs the functions in the herein exemplary embodiments of the invention. In addition, while a particular feature of the invention may have been disclosed with respect to only one embodiment, such feature may be combined with one or more other features of other embodiments as may be desired or advantageous for any given or particular application.

What is claimed is:

1. A yeast preparation method comprising the steps of:
   a. providing at least one bag comprising at least one pathway for the introduction of air and for exhausting gases;
   b. installing said at least one bag into a skid unit with a means for separating and sealing the at least one bag;
   c. propagating yeast within said at least one bag;
   d. concentrating said yeast in a small section of said at least one bag; and
   e. separating and sealing, using the means of step b, said small section of said at least one bag from said at least one bag, while not exposing the yeast in said small section of said at least one sealed bag to contamination.

2. The yeast preparation method of claim 1 wherein the separation and sealing of said at least one bag is by use of a platen.

3. The yeast preparation method of claim 1 further comprising the step of introducing air to aerate the yeast within said at least one bag during said propagating step.

4. The yeast preparation method of claim 1 wherein said at least one bag has a bottom and wherein concentrating step is accomplished by allowing said yeast to settle to the bottom of said at least one bag under the force of gravity.

5. The yeast preparation method of claim 1 further comprising the step of cooling the yeast in said at least one bag to a temperature at which further yeast propagation is retarded, the cooling step occurring subsequent to the propagating step.

6. The yeast preparation method of claim 5 wherein said cooling step is accomplished by cooling panels which squeeze said at least one bag on at least two sides.

7. The yeast preparation method of claim 1 further comprising the step of maintaining the yeast in said small section of said at least one bag at a temperature, which retards further yeast propagation.

8. The yeast preparation method of claim 1 further comprising the steps of:
   a. introducing wort into said at least one bag;
   b. cooling said wort to a temperature conducive to yeast propagation; and
   c. inoculating said wort.

9. The yeast preparation method of claim 8 further comprising the step of cooling the yeast in said at least one bag to a temperature at which further yeast propagation is retarded, the cooling step occurring subsequent to the propagating step.

10. The yeast preparation method of claim 8 further comprising the step of attaching to said at least one bag, a bag fitting adapted to provide said at least one pathway, and wherein said at least one pathway is utilized in said introducing step and said inoculating step.

11. The yeast preparation method of claim 10 further comprising the step of forcing air through said at least one pathway to aerate the contents of said at least one bag during said propagating step.

12. The yeast preparation method of claim 11 further comprising the step of attaching said at least one bag fitting to a valve manifold comprising a plurality of hoses.

* * * * *